United States Patent [19]

Radovich et al.

[11] Patent Number: 5,069,788
[45] Date of Patent: Dec. 3, 1991

[54] MULTI-PASS BLOOD WASHING AND PLASMA REMOVAL DEVICE AND METHOD

[75] Inventors: John M. Radovich; Richard W. Schofield, both of Bend, Oreg.

[73] Assignee: Pfizer Hospital Products Groups, Inc., New York, N.Y.

[21] Appl. No.: 657,124

[22] Filed: Feb. 19, 1991

Related U.S. Application Data

[62] Division of Ser. No. 398,065, Aug. 24, 1989, Pat. No. 5,017,293.

[51] Int. Cl.$^5$ .................. B01D 61/28; B01D 63/04
[52] U.S. Cl. ......................... 210/321.8; 210/321.89; 210/500.23

[58] Field of Search .......... 210/321.6, 321.72, 321.78, 210/321.79, 321.8, 321.81, 321.87, 321.88, 321.89, 321.9, 500.23

[56] References Cited

U.S. PATENT DOCUMENTS 4,729,829  3/1988  Duggins ........................ 210/321.8

Primary Examiner—Frank Sever
Attorney, Agent, or Firm—Chernoff, Vilhauer, McClung & Stenzel

[57] ABSTRACT

A blood washing and plasma separation device and method are disclosed, which utilize lumen-side fed hollow fiber membranes in multiple separation passes in conjunction with countercurrent flow wash injection.

8 Claims, 2 Drawing Sheets

MULTI-PASS BLOOD WASHING AND PLASMA REMOVAL DEVICE AND METHOD

This is a divisional of copending application Ser. No. 07/398,065 filed on Aug. 24, 1989, now U.S. Pat. No. 5,017,293.

BACKGROUND OF THE INVENTION

Filtration devices for the treatment of blood are known. For example, U.S. Pat. No. 4,498,990 discloses a cellular blood component/plasma separation device comprising two hollow fiber bundles situated coaxially to each other in a housing having blood inlet and outlet ports, a filtrate outlet port, and a replacement liquid port for supplying plasma makeup of undisclosed composition (probably proteins and sugars) to the treated blood prior to its reintroduction to the donor. U.S. Pat. No. 4,668,399 discloses a single-pass nonwashing plasmapheresis module and process for use on whole blood (having a Hematocrit of about 35–45) having short hollow fibers with an effective length to lumen diameter ratio of not greater than 300 in a steady state flow mode and not greater than about 540 in a pulsed flow mode. U.S. Pat. No. 31,688 also discloses a nonwashing single pass plasmapheresis non-hollow fiber membrane device. U.S. Pat. No. 4,631,050 discloses a batch autotransfusion system that, following macrofiltration of a patient's whole blood and prior to a planar membrane separation of the plasma and cellular components, permits batch washing of the blood by mechanical agitation with saline solution. U.S. Pat. No. 4,565,626 discloses a device for removing toxins from blood that contacts the blood for a period of time with adsorbent material packed between hollow fibers, then withdraws the blood from the adsorbent; saline solution is used as a pressure-transmitting medium. Finally, U.S. Pat. No. 4,038,190 discloses a fluid fractionation apparatus having two fiber bundles in series with an externally-supplied fluid inlet port that permits a fluid to be supplied to the outside (as opposed to the lumen side) of the hollow fibers.

However, none of the foregoing devices addresses the need for an efficient combination blood component washing, concentration and separation device capable of performing such operations in a continuous mode, and capable of operating on both whole and diluted blood, the latter being encountered in surgical cavities as a result of the use during surgery of saline wash to cleanse the surgical field.

The present invention meets such a need, thus providing a significant advance in the art of blood filtration and treatment, as well as providing other advantages and efficiencies which will become apparent from the detailed description which follows.

SUMMARY OF THE INVENTION

There are essentially two aspects to the present invention. In one aspect, there is provided a combination cellular blood component washing and plasma removing device comprising elongate microporous hollow fiber membranes arranged into at least two discrete fiber bundles, the hollow fiber membranes permitting the permeation of at least a portion of non-cellular blood components through the walls thereof while preventing the permeation of cellular blood components, a housing containing the fiber bundles, the housing having a blood inlet port, a plasma-depleted outlet port, a plasma permeate port, and washing means for contacting cellular blood components with wash fluid and for removing the wash fluid from the housing prior to the exit of cellular blood components from the plasma-depleted outlet port, wherein the lumens of the hollow fiber membranes of the fiber bundles are in fluid communication with each other; the blood inlet port, the plasma-depleted outlet port, and the washing means are all in fluid communication with the lumens of the hollow fiber membranes of the fiber bundles; and the plasma permeate port is in fluid communication with the outside of the hollow fiber membranes of the fiber bundles.

In the other aspect, the present invention provides a method of simultaneously washing and concentrating cellular blood components and removing plasma from fluid blood having a Hematocrit (Hct) as low as 15 (such as is encountered in surgical cavities during the course of surgery) comprising the steps of feeding fluid blood under pressure to the lumens of elongate microporous hollow fiber membranes arranged into at least two discrete fiber bundles, the hollow fiber membranes permitting the permeation of at least a portion of non-cellular blood components through the walls thereof while preventing the permeation of cellular blood components, the lumens of the hollow fiber membranes of the fiber bundles being in fluid communication with each other; contacting the blood with wash fluid at least one point between discrete fiber bundles; withdrawing a fluid containing wash fluid and non-cellular blood components, including plasma, from the outside of the walls of the hollow fiber membranes; and withdrawing a fluid containing cellular blood components in concentrated form from the lumens of the hollow fiber membranes of the last of the discrete fiber bundles.

The foregoing and other objectives, features, and advantages of the invention will be more readily understood upon consideration of the following detailed description of the invention, taken in conjunction with the accompanying drawings.

DETAILED DESCRIPTION OF THE INVENTION

According to the present invention, there is provided a multi-pass module, the essential features of which comprise at least two discrete hollow fiber bundles arranged in series to separate blood plasma and cellular components with countercurrent cellular component washing means between said bundles.

The hollow fiber membranes are fed whole or diluted blood through the lumens thereof to permit the permeation of at least a portion of non-cellular (plasma) blood components through the walls thereof, while preventing the permeation of cellular blood components, thereby effecting separation of plasma and cellular components. Wash fluid is introduced into the module at at least one point in fluid communication with the lumens of the hollow fibers to contact the cellular blood components with turbulence, causing a washing of the same.

Figure 1:
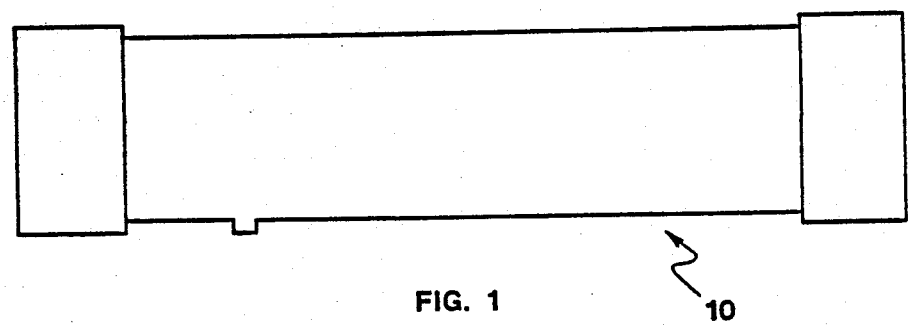
FIG. 1 is a side view of an exemplary module embodying the features of the present invention.
Figure 2:
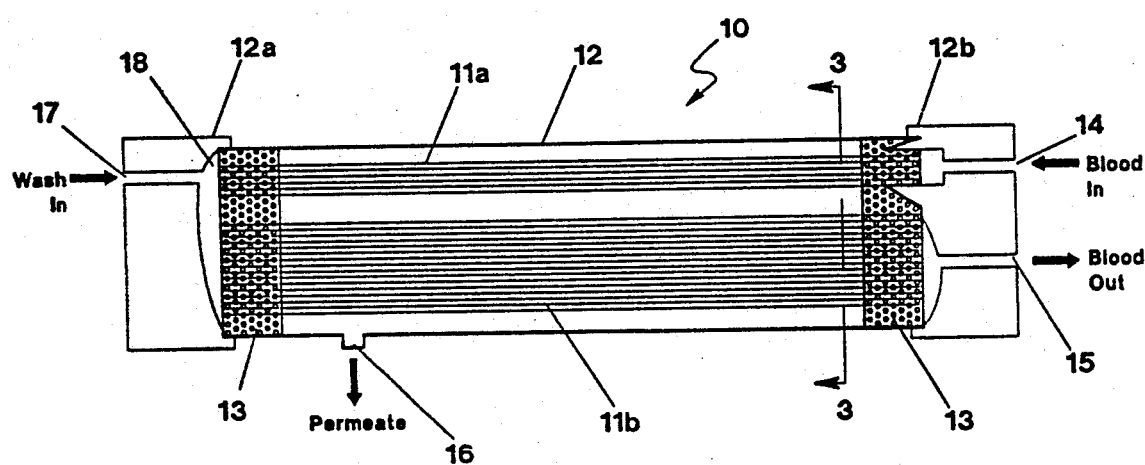
FIG. 2 is a longitudinal cross section of an exemplary two-pass, one-wash module of FIG. 1.
Figure 3:
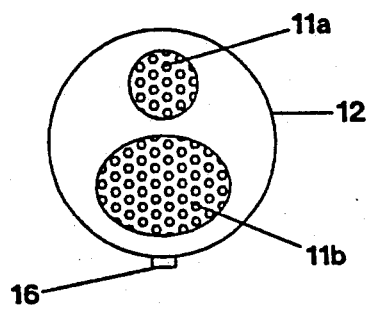
FIG. 3 is a cross section of FIG. 2 taken on the line 3—3.

Referring now to the drawings, wherein like numerals denominate the same elements, FIGS. 1-3 show various views of an exemplary two-pass, one wash, blood washing and plasma removal device 10 of the present invention. Referring in particular to FIG. 2, the device 10 comprises two bundles 11a and 11b of elongate microporous hollow fiber membranes which are selective to the permeation of non-cellular blood components and prevent permeation of cellular blood components. The bundles 11a and 11b are contained by a chamber or housing 12 and secured thereto by thermoplastic or thermosetting potting material 13. Housing end caps 12a and 12b are either integral with housing 12 or removable for ease of manufacture and cleaning. The housing, comprising elements 12, 12a and 12b, has a blood inlet port 14, a plasma-depleted outlet port 15, a plasma permeate port 16, and a wash inlet port 17 and associated plenum 18. Note that the arrangement of elements permits the inside or lumens of the hollow fiber membranes of both bundles 11 to be in fluid communication with each other, and that the lumens are also in fluid communication with blood inlet port 14, with plasma-depleted outlet port 15, with wash fluid inlet port 17 and with the fluid inlet port's associated plenum 18; plasma permeate port 16 is in fluid communication with the outside of the hollow fiber membranes of both bundles 11.

Figure 4:
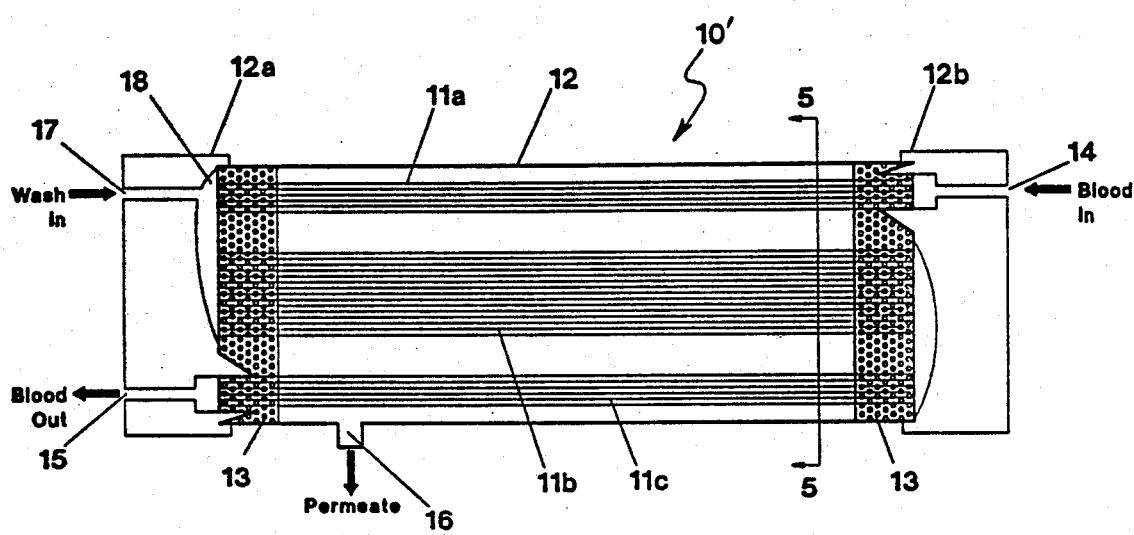
FIG. 4 is a longitudinal cross section of an exemplary three-pass, one wash module of FIG. 1.
Figure 6:
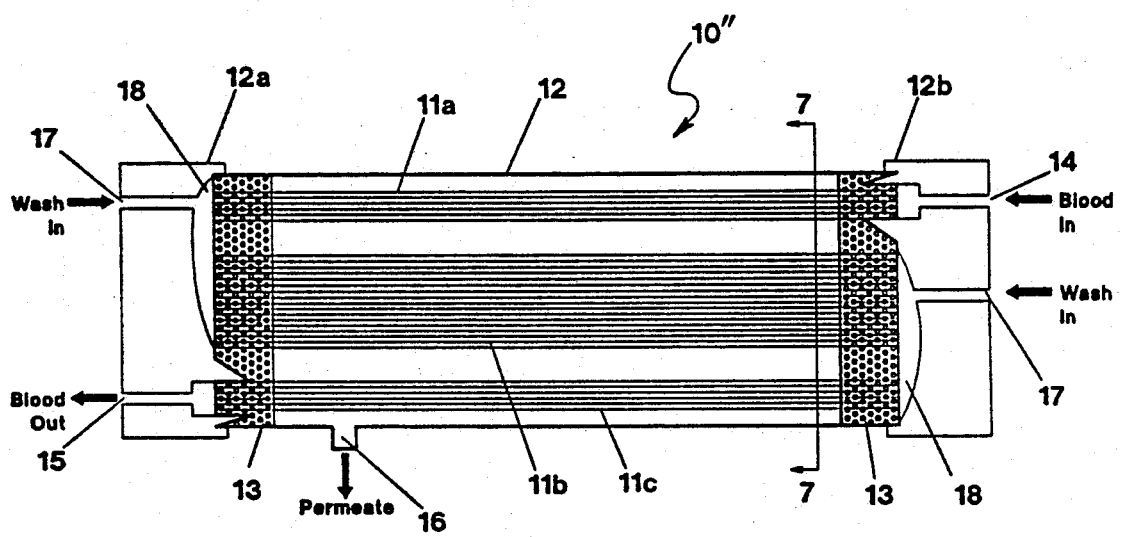
FIG. 6 is a longitudinal cross section of an exemplary three-pass, two-wash module of FIG. 4.
Figure 5:
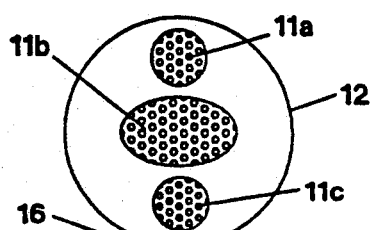
FIG. 5 is a cross section of FIG. 4 taken on the line 5—5.
Figure 7:
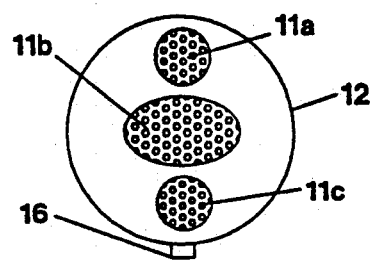
FIG. 7 is a cross section of FIG. 6 taken on the line 7—7.

FIGS. 4-5 show two cross sectional views of an exemplary three-pass, one wash, blood washing and plasma removal device 10' of the present invention, while FIGS. 6-7 show the same views of an exemplary three-pass, two wash, blood washing and plasma removal device 10" of the present invention both 10' and 10" having a third hollow fiber bundle 11c. Although only two- and three-pass modules are shown in drawings herein, it should be understood that the present invention contemplates inclusion of designs having more than three passes through hollow fiber membranes, the number of passes being equal to n, where n is $\geq 2$; the number of washes contemplated is (n-m), where m is 1 or 2, with the limitation that (n-m) $\geq 1$.

Suitable hollow fiber membranes 11 may be described as semipermeable, hydrophilic, polymeric and microporous. Hydrophobic fibers that have been rendered hydrophilic by chemical or physical treatment are acceptable as well. Examples include those made of treated polypropylene, polyethylene, polyvinyl alcohol, polyvinylidenefluoride, polymethylmethacrylate, and polysulfone. Internal diameter (ID) of such hollow fiber membranes is preferably in the range of 200-400 microns, wall thickness is 50-150 microns, while average pore size is preferably in the range of 0.1 to 1.0 micron, and porosity is from 25% to 80%. Fiber length is preferably between 30 and 100 cm, while the ratio of effective fiber length (L) to diameter (D) of the lumens is from about 1000 to about 5000. A preferred potting material 13 is polyurethane, for example, BIOTHANE 228, available from CasChem of Bayonne, N.J.

In operation, with reference to FIG. 2, blood having a Hematocrit as low as 15, such as is encountered in diluted blood salvaged from a surgical cavity, is fed via blood inlet port 14, to the lumens of the first bundle of hollow fiber membranes, either under pressure or, alternatively, a vacuum is applied to the outside or "shell" side of the fibers via plasma permeate port 16, to create a transmembrane pressure (TMP) of from 100 to 500 mmHg. The flow rate is adjusted to a preferred rate of 100 ml/min, measured at the blood outlet port 15. Plasma, plasma proteins, dissolved solutes, and any saline wash from a surgical cavity, comprising noncellular components of the blood, permeate from the lumens through the walls to the shell side of the first bundle of fibers 11a, ultimately passing out of the module via permeate port 16. A portion of the blood rich in cellular blood components (principally red and white blood cells and platelets, together with some hemoglobin and plasma proteins), continues its passage through the lumens of the first bundle of fibers, thence into plenum 18, where it encounters wash solution entering the module via wash port 17 and its associated plenum 18. The introduction of wash solution in a flow which is initially countercurrent to the flow of blood causes a turbulence between the two, resulting in a washing of the cellular components and a dilution of hemoglobin from red blood cells. Because of the overall direction of flow and the applied transmembrane pressure, the cellular component-rich blood, along with the injected wash solution, enters the lumens of the second bundle of fibers 11b where further concentration of the cellular blood components takes place by additional permeation and removal of non-cellular components, including the injected saline wash; in addition, a portion of dissolved hemoglobin permeates the walls of the fibers and is separated via permeate port 16. Washed and concentrated blood having a substantially increased Hematocrit exits via blood outlet port 15.

The same principles of operation apply to the exemplary embodiments of the invention shown in FIGS. 4 and 6, with the exception that two countercurrent wash injection ports and associated plenums are used in the embodiment shown in FIG. 6.

EXAMPLE 1

A two-pass, one wash module of substantially the same design as shown in FIG. 2 and having 4.5 ft$^2$ of membrane surface area was prepared with treated hydrophilic polypropylene hollow fiber membranes totaling approximately 90 cm in length, an ID of 330 microns, an average pore size of 0.6 micron, and a 70% porosity. The total, effective L:D ratio was about 2700. The potting compound used was a blood-compatible polyurethane, and blood and wash ports and plenums 14, 15, 17 and 18 were molded into end caps 12a and 12b. Dilute blood with an Hct of 22 and a hemoglobin concentration (Hb) of 311 mg/dl was introduced to the lumens of the fibers of fiber bundle 11a via blood inlet port 14 at an average flow rate of 61 ml/min. The average flow rate, measured at the blood outlet port 15, was 18 ml/min, and an average TMP of 260 mmHg was induced by the application of a vacuum at permeate port 16. Sterile normal saline solution was continuously introduced into wash port 17 and associated plenum 18 at the average rate of 14 ml/min. Plasma recovery from the plasma permeate port was calculated to be 89% of the plasma in the feed blood, Hb was 93 mg/dl, while the Hct of blood collected from blood exit port 15 was 64, representing a three-fold increase in Hct.

EXAMPLE 2

Whole blood having an Hct of 40 treated with the device of Example 1 with substantially the same flow rates and TMP, yields a calculated Hct of 75 as measured at blood exit port 15. Plasma recovery is calculated to be 78%.

EXAMPLE 3

A three-pass, one wash module of substantially the same configuration as shown in FIG. 4 was prepared in the same manner and with the same membranes as in Example 1. The membranes of this Example, totaling approximately 45 cm in length, had a total, effective L:D ratio of about 1360.

Dilute blood feed with an Hct of 21 was introduced to the lumens of the fibers of fiber bundle 11a via blood inlet port 14 at an average flow rate of 72 ml/min. The average flow rate of the blood product, measured at the blood outlet port 15, was 33 ml/min, and an average TMP of 310 mmHg was induced by the application of a vacuum at permeate port 16. Sterile, normal saline solution was continuously introduced into wash port 17 and associated plenum 18 at the average rate of 29 ml/min. Plasma recovery from plasma permeate port 16 was calculated to be 68%, while the Hct of blood collected from blood outlet port 15 was 46, representing greater than a two-fold increase in Hct. Hb in the blood feed was 385 mg/dl, while the Hb in the blood product was 223 mg/dl.

EXAMPLE 4

A three-pass, two wash module of substantially the same design as shown in FIG. 6 and having 6.8 ft$^2$ of membrane surface area may be prepared in the same manner and with the same membranes as in Example 1, totaling approximately 135 cm in length, and having a total effective L:D ratio of about 4100. Dilute blood feed with an Hct of 21 is introduced to the lumens of the fibers of fiber bundle 11a via blood inlet port 14 at an average flow rate of 128 ml/min. The average flow rate of the blood product, measured at the blood outlet port 15, is 45 ml/min, and an average TMP of 360 mmHg is induced by the application of a vacuum at permeate port 16. Sterile, normal saline solution is continuously introduced into wash ports 17 and associated plenums 18 at the average rates of 236 and 185 ml/min. Plasma recovery from plasma permeate port is calculated to be 82% while the Hct of blood collected from blood outlet port 15 is calculated to be 60, representing a threefold increase in Hct. Hb in the blood feed is 1002 mg/dl, while the calculated Hb in the blood product is 118 mg/dl.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A combination cellular blood component washing and plasma removing device comprising means for enabling continuous washings concentration and separating including
    (a) elongate microporous hollow fiber membranes arranged into at least two discrete fiber bundles, said hollow fiber membranes permitting the permeation of at least a portion of non-cellular blood components through the walls thereof while preventing the permeation of cellular blood components,
    (b) a housing containing said fiber bundles, said housing having a blood inlet port, a plasma-depleted outlet port, a plasma permeate port, and washing means for contacting said cellular blood components with wash fluid and for removing said wash fluid from said housing prior to the exit of said cellular blood components from said plasma-depleted outlet port, wherein the lumens of the hollow fiber membranes of said fiber bundles are in fluid communication with each other; said blood inlet port, said plasma-depleted outlet port, and said washing means are all in fluid communication with the lumens of the hollow fiber membranes of said fiber bundles; and said plasma permeate port is in fluid communication with the outside of the hollow fiber membranes of said fiber bundles.

2. The device of claim 1 wherein said washing means comprises at least one wash fluid inlet port and associated plenum adapted to permit mixing of said wash fluid with said blood.

3. The device of claim 2, having two discrete fiber bundles and one wash fluid inlet port with an associated plenum.

4. The device of claim 2, having three discrete fiber bundles and one wash fluid inlet port with an associated plenum.

5. The device of claim 2, having three discrete fiber bundles and two wash fluid inlet ports with associated plenums.

6. The device of claim 5 wherein said two fluid inlet ports and associated plenums are at opposing ends of said fiber bundles.

7. The device of claim 2 wherein the ratio of effective fiber length to diameter of the lumens for said hollow fiber membranes is from about 1000 to about 5000.

8. The device of claim 1 wherein the ratio of effective fiber length to diameter of the lumens for said hollow fiber membranes is from about 1000 to about 5000.

* * * * *